United States Patent [19]

Cianci

[11] 4,417,891
[45] Nov. 29, 1983

[54] COLLECTION DEVICE WITH ANTISEPTIC LIQUID FOR BODY FLUIDS

[75] Inventor: James P. Cianci, Cary, Ill.

[73] Assignee: The Kendall Company, Boston, Mass.

[21] Appl. No.: 309,625

[22] Filed: Oct. 8, 1981

[51] Int. Cl.³ .............................................. A61M 1/00
[52] U.S. Cl. .................................. 604/317; 128/760; 128/767
[58] Field of Search ................... 128/272, 272.1, 272.3, 128/DIG. 24, 760, 295, 762, 766, 767, 768; 222/212, 207, 209; 422/5, 28, 37; 604/317, 323, 322, 326, 323, 327, 335, 345, 349, 350

[56] References Cited

U.S. PATENT DOCUMENTS

| | | | |
|---|---|---|---|
| 2,054,535 | 9/1936 | Diack | 128/283 |
| 2,800,905 | 7/1957 | Simmons et al. | 128/DIG. 24 |
| 3,175,736 | 3/1965 | Pelto | 222/207 |
| 3,601,119 | 8/1971 | Engelscher | 604/323 |
| 3,690,320 | 9/1972 | Riely | 128/283 |
| 3,818,910 | 6/1974 | Harris | 128/232 |
| 4,203,443 | 5/1980 | Genese | 128/272.3 |
| 4,229,408 | 10/1980 | Bennett et al. | 422/5 |
| 4,259,952 | 4/1981 | Avoy | 128/272.3 |
| 4,261,474 | 4/1981 | Cohen | 215/250 |
| 4,265,243 | 5/1981 | Taylor | 128/275 |
| 4,319,573 | 3/1982 | Whitlock | 604/328 |
| 4,325,368 | 4/1982 | Kaemmerer | 128/272.1 |

FOREIGN PATENT DOCUMENTS

| | | | |
|---|---|---|---|
| 1010029 | 3/1952 | France | 128/272.3 |
| 8002706 | 12/1980 | PCT Int'l Appl. | 128/760 |

OTHER PUBLICATIONS

Gore-Tex Membrane Products "Catalog Cat", W. L. Gore & Assoc., Inc. Elkton, Md. 21921.

*Primary Examiner*—C. Fred. Rosenbaum
*Assistant Examiner*—J. L. Kruter
*Attorney, Agent, or Firm*—Powell L. Sprunger

[57] ABSTRACT

A device for collecting body fluids from a patient comprising, a container having a chamber to receive the body fluids. The device has a receptacle permanently secured to a wall of the container and having a cavity to receive a liquid agent, with the receptacle cavity communicating with the container chamber through a relatively small opening adjacent a lower portion of the cavity. The receptacle has an aperture in an upper portion of the receptacle communicating between the cavity and the outside of the receptacle.

8 Claims, 6 Drawing Figures

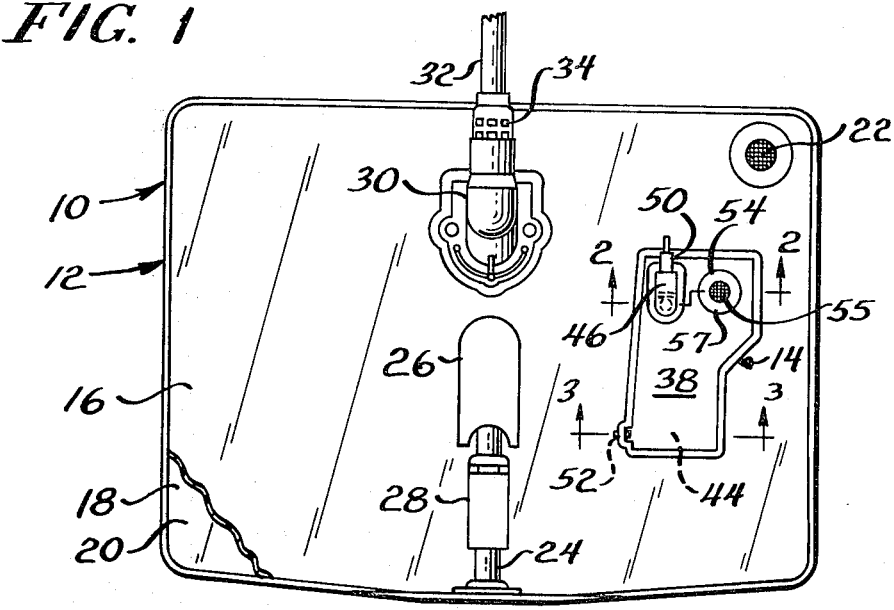
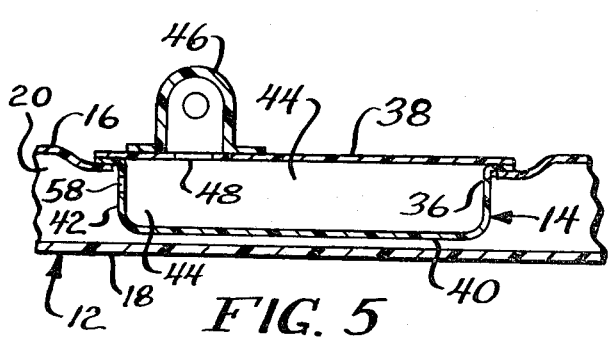
FIG. 1
FIG. 2
FIG. 3
FIG. 4
FIG. 5

4,417,891

COLLECTION DEVICE WITH ANTISEPTIC LIQUID FOR BODY FLUIDS

BACKGROUND OF THE INVENTION

The present invention relates to devices for collecting body fluids from a patient.

Before the present invention, a number of collection bags have been proposed to receive urine from a patient. A catheter is placed in the patient such that it communicates with the patient's bladder, and during catheterization urine drains from the bladder through the catheter and a drainage tube to the collection bag for retention therein. Such systems should be closed to the atmosphere to minimize the possibility of contamination. Nonetheless, a persistent problem has been found in that the collected urine in the bag may become contaminated, resulting in possible undesired retrograde bacteria movement through the system to the bladder of the patient.

SUMMARY OF THE INVENTION

A principal feature of the present invention is the provision of an improved device for collecting body fluids from a patient.

The device comprises, a container having a chamber to receive the body fluids. The device has a receptacle permanently secured to a wall of the container and having a cavity to retain a liquid agent, with the receptacle cavity communicating with the container chamber through a relatively small opening adjacent a lower portion of the cavity. The receptacle has opening means in an upper portion of the receptacle communicating between the cavity and the outside of the receptacle. The receptacle has valve means communicating with an upper portion of the receptacle cavity.

A feature of the present invention is that the liquid agent may be placed in the receptacle cavity through the valve means.

Another feature of the invention is that the opening means causes flow of the liquid agent from the receptacle cavity to the container chamber for mixture with the collected body fluids.

Still another feature of the invention is that the agent comprises a liquid antiseptic agent introduced into the collected body fluids in order to minimize the possibility of bacterial growth in the body fluids.

Further features will become more fully apparent in the following description of the embodiments of this invention and from the appended claims.

DESCRIPTION OF THE DRAWINGS

In the drawings:

FIG. 1 is a fragmentary front plan view of a collection device of the present invention;

FIG. 2 is a fragmentary sectional view taken substantially as indicated along the line 2—2 of FIG. 1;

FIG. 3 is a fragmentary sectional view taken substantially as indicated along the line 3—3 of FIG. 1;

FIG. 4 is a fragmentary sectional view of another embodiment of the device of the present invention;

FIG. 5 is a fragmentary sectional view of another embodiment of the device of the present invention.

DESCRIPTION OF THE PREFERRED EMBODIMENTS

Figure 6:
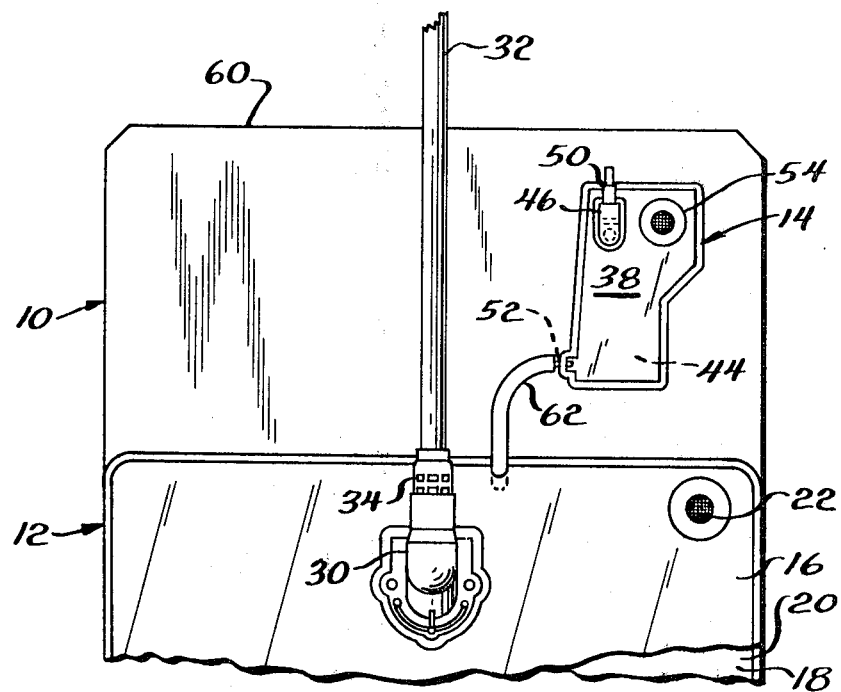
FIG. 6 is a fragmentary front plan view of another embodiment of the collection device of the present invention.

Referring now to FIGS. 1–3, there is shown a device generally designated 10 for collecting body fluids comprising a container 12 and a receptacle 14. The container 12 has a front wall 16 and a back wall 18 of suitable flexible plastic material joined together at the edges of the front and back walls 16 and 18 to define a chamber 20 in the container 12. The container 12 may have a vent 22 with a bacteria filter of known type, such as a woven fiberglass material, to filter bacteria passing from the atmosphere into the container chamber 20. The container 12 may have a discharge tubular section 24 attached to a lower portion of the container front wall 16 and communicating with the chamber 20, with an outer end of the tubular section 24 being received in a pocket 26 on the front wall 16 in a storage position of the tubular section 24. The tubular section 24 may have a suitable clamp 28 which prevents passage of urine through the tubular section 24 when the clamp 28 is closed. When it is desired to drain urine from the container chamber 20, the outer end of the tubular section 24 is removed from the pocket 26 and the clamp 28 is opened in order to permit passage of urine through the tubular section 24, after which the clamp 28 is closed and the tubular section 24 is again inserted into the pocket 26 in the storage position of the tubular section 24.

The container 12 may have a hollow connector 30 in the form of a drip chamber attached to the front wall 16 of the container 12 and communicating with the container chamber 20. As shown, the upper portion of the connector 30 is attached to the downstream end of a drainage catheter tube 32, such that the drainage tube 32 communicates with the connector 30. If desired, the connector 30 may have a vent 34 with a bacteria filter of known type, such as a woven fiberglass material, to filter bacteria from air passing from the atmosphere into the connector 30 through the vent 34. In use, a catheter (not shown) is passed through the urethra of a patient until the catheter communicates with the patient's bladder, and a proximal end of the catheter extending outside the patient is attached to the upstream end of the drainage tube 32. During catheterization, urine drains through the catheter, drainage tube 32, and the connector 30 into the container chamber 20 for collection therein. Although the described system is closed to the atmosphere, it has been found that bacteria may form in the collected urine in the chamber 20.

The front wall 16 of the container 12 has an enlarged opening 36, and the receptacle 14 is received in the opening 36 with a portion of the receptacle 14 located in the container chamer 20. As shown, the receptacle 14 is attached to the container front wall 16 peripherally around the opening 36 by suitable means, such as by adhesive. The receptacle 14 has a front wall 38 generally aligned with the front wall 16 of the container 12, a back wall 40 located in the container chamber 20, and a side wall 42 connecting the front and back walls 38 and 40 and extending peripherally around the receptacle 14, such that the front wall 38, the back wall 40, and the side wall 42 define a cavity 44 in the receptacle 14. In a preferred form, the walls of the receptacle 14 are made from a relatively rigid plastic material.

The receptacle 14 has a hollow connector 46 attached to the front wall 38, such that the connector 46 communicates with the cavity 44 through an aperture 48 in the front wall 38. Also, the receptacle has a valve assembly 50 attached to an upper portion of the connector 46. The valve assembly 50 is of known type and actuates to the open position responsive to contact of the valve assembly 50 by the tip of a syringe.

The receptacle 14 has a tubular section 51 defining a relatively small opening 52 communicating between the receptacle cavity 44 and the container chamber 20. The receptacle opening 52 is located adjacent a lower portion of the cavity 44, and is sufficiently small, such as 0.030 inches in diameter, such that the surface tension of liquid contained in the cavity 44 will impede liquid drainage from the cavity 44 to the chamber 20. In other words, the internal diameter of the receptacle opening 52 and the surface tension of liquid contained in the cavity 44 are so interrelated as to insure impeded passage of liquid from cavity 44, through opening 52, to container chamber 20. In an alternative form, as shown in FIG. 4, the tubular section 51 has a porous plug 53, such as sintered polyethylene positioned in the opening 52. With reference to FIGS. 1–3, the receptacle 14 has a vent 54 communicating between an upper portion of the cavity 44 and the atmosphere. The vent 54 has a circular bacteria filter element 55, such as a woven fiberglass material, secured to the receptacle 14 over an opening 56 by an annular plastic ring 57 which is attached to the receptacle 14 by suitable means, such as by adhesive.

In use of the device 10, the tip of a syringe (not shown) is attached to the valve assembly 50 in order to actuate the valve assembly 50 and open the valve assembly 50 to permit a liquid antiseptic agent, such as povidone iodine, to be pumped by the syringe through the valve means 50 and the connector 46 into the receptacle cavity 44. The vent 54 will permit passage of air from the atmosphere into the cavity 44 while filtering bacteria from the air by the filter element 55. The vented cavity 44 permits slow passage of the antiseptic agent through the opening 52 into the container chamber 20, with the rate of liquid flow being controlled by the size of openings 52 and 56. In turn, the antiseptic agent introduced into the collected urine minimizes the possibility of bacterial growth in the urine. In this manner, the collection device of the present invention minimizes the possibility of contamination to the patient's bladder which may be caused by retrograde bacterial movement from the collected urine through the drainage tube 32 to the patient.

Another embodiment of the present invention is illustrated in FIG. 5, in which like reference numerals designate like parts. In this embodiment, the receptacle 14 has an aperture 58 communicating between an upper portion of the cavity 44 and the chamber 20 to permit passage of air from the chamber 20 to the cavity 44 and release of the antiseptic agent from the lower part of the cavity 44 to the chamber 20. Hence, in this embodiment, the receptacle need not have a vent to the atmosphere.

Another embodiment of the present invention is illustrated in FIG. 6, in which like reference numerals designate like parts. In this embodiment, the device 10 has a container 12 with walls 16 and 18 defining a chamber 20, and a receptacle 14 with cavity 44, connector 46, valve assembly 50, vent 54, and small opening 52, as previously described. However, in this embodiment, the container 12 has a header 60 of relatively rigid plastic material located above the container chamber 20. As shown, the receptacle 14 is attached to the header 60, and the device 10 has a tubular section 62 which communicates between the opening 52 of the receptacle 14 and an upper portion of the container chamber 20. The device operates as previously described in connection with the device of FIGS. 1–3. An antiseptic agent may be introduced through the valve means 50 into the receptacle cavity 44, and the vent 54 causes passage of the antiseptic agent through the opening 52 and tubular section 62 into the container chamber 20 where it minimizes the possibility of bacterial growth in the collected urine.

The foregoing detailed description is given for clearness of understanding only, and no unnecessary limitations should be understood therefrom, as modifications will be obvious to those skilled in the art. For example, a liquid deodorizing agent may be placed in the receptacle cavity 44 either alone or with an antiseptic agent. The deodorizing agent may be introduced into container chamber 20 to minimize odors of the collected urine.

I claim:

1. A device for collecting urine from a patient comprising:
   a container having flexible walls with inner and outer surfaces, a drainage catheter, a discharge tube and a chamber to receive urine;
   a receptacle permanently secured to an outer surface of a wall of the container and having a cavity, a vent means through an upper portion of said cavity open to ambient atmosphere, the vent means including a bacteria filter, the receptacle cavity communicating with the container chamber directly through an opening means of approximately 0.030 inches in diameter, through a lower portion of said cavity, the internal diameter of the opening means and the surface tension of liquid contained within the cavity being so interrelated as to insure impeded passage of liquid from the cavity, through the opening means, to the container; and
   an antiseptic agent means in liquid form in said cavity, the passage of said agent through said opening means from the cavity to the chamber being facilitated by said vent means open to the ambient atmosphere, the antiseptic agent means in the container chamber minimizing the possibility of contamination to the patient's bladder caused by retrograde bacteria movement from the device to the patient through the drainage tube.

2. The device of claim 1 wherein the receptacle has rigid walls defining said cavity.

3. The device of claim 1 including valve means communicating between the receptacle cavity and the atmosphere to permit placement of said agent in the cavity.

4. The device of claim 1 wherein the container has a pair of opposed flexible walls defining said chamber.

5. The device of claim 1 including a porous material in said opening.

6. A device for collecting urine from a patient comprising:
   a container having flexible walls with inner and outer surfaces, a drainage catheter, a discharge tube and a chamber to receive urine;
   a receptacle permanently secured to a wall of the container and having a cavity, aperture means through an upper portion of said cavity open to said chamber, the receptacle cavity communicating directly through an opening means of approximately 0.030 inches in diameter through a lower portion of said cavity, the internal diameter of the opening means and the surface tension of liquid contained within the cavity being so interrelated as to insure impeded passage of liquid from the cavity, through the opening means, to the container; and an antiseptic agent means in liquid form in said cavity, the passage of said agent through said opening means from the cavity to the chamber being facilitated by said aperture means open to said chamber, the antiseptic agent means in the container chamber minimizing the possibility of contamination to the patient's bladder caused by retrograde bacteria movement for the device to the patient through the drainage tube.

7. The device of claim 1 wherein a wall of the container includes a rigid header above the chamber, said receptacle being permantently secured to said rigid header.

8. The device of claim 7 including valve means communicating between an upper portion of the cavity and the atmosphere to permit placement of said agent in the cavity.

* * * * *